(12) United States Patent
Xing et al.

(10) Patent No.: US 10,392,672 B2
(45) Date of Patent: Aug. 27, 2019

(54) YEAST STRAIN AND METHOD FOR PRODUCING NATURAL CINNAMIC ACID USING THE YEAST STRAIN FOR FERMENTATION

(71) Applicant: XIAMEN OAMIC BIOTECHNOLOGY CO., LTD., Xiamen (CN)

(72) Inventors: Chenguang Xing, Xiamen (CN); Xijing Zhao, Xiamen (CN); Zhiqiang Huang, Xiamen (CN); Cuiping Chen, Xiamen (CN); Wei Liu, Xiamen (CN)

(73) Assignee: XIAMEN OAMIC BIOTECHNOLOGY CO., LTD., Xiamen (CN)

( * ) Notice: Subject to any disclaimer, the term of this patent is extended or adjusted under 35 U.S.C. 154(b) by 0 days.

(21) Appl. No.: 15/574,767

(22) PCT Filed: Jan. 13, 2016

(86) PCT No.: PCT/CN2016/070787
§ 371 (c)(1),
(2) Date: Nov. 16, 2017

(87) PCT Pub. No.: WO2017/008482
PCT Pub. Date: Jan. 19, 2017

(65) Prior Publication Data
US 2018/0148802 A1    May 31, 2018

(30) Foreign Application Priority Data
Jul. 14, 2015  (CN) .......................... 2015 1 0411874

(51) Int. Cl.
*C12N 1/16* (2006.01)
*C12P 7/40* (2006.01)
*C12R 1/645* (2006.01)

(52) U.S. Cl.
CPC ................ *C12R 1/645* (2013.01); *C12N 1/16* (2013.01); *C12P 7/40* (2013.01)

(58) Field of Classification Search
None
See application file for complete search history.

(56) References Cited

U.S. PATENT DOCUMENTS

2005/0148054 A1* 7/2005 Qi ........................... C12N 9/88
                                                             435/108

FOREIGN PATENT DOCUMENTS

| CN | 104131017 A | 11/2014 |
| CN | 105087387 A | 11/2015 |
| JP | S62248493 A | 10/1987 |

OTHER PUBLICATIONS

Koichi Ogata et al., "Metabolism of Aromatic Amino Acid in Microorganisms Part 1. Formation of Cinnamic Acid from Phenylalanine", Agricultural and Biological Hemistry, Sep. 9, 2014; 31:2, 200-206; pp. 200-206.

Liang, Jinglong et al., "Construction of Genetically Engineering *Escherichia coli* for Cinnamic Acid Production", Academic Conference on "New Technology and New Development of Food Industry" and the Proceeddings of the Annual Conference of Guangdong Institute of Food Science and Technology in 2014, Nov. 30, 2014, pp. 29-31.

* cited by examiner

Primary Examiner — Christian L Fronda
(74) Attorney, Agent, or Firm — Rabin & Berdo, P.C.

(57) ABSTRACT

The present invention relates to a strain of *Rhodotorula* sp. OMK-1(CCTCC M 2015326) and a method for producing natural cinnamic acid through the fermentation of *Rhodotorula* sp. OMK-1. The production method comprises steps of strain activation, seed culture, fermentation, extraction, etc. The fermentation process uses natural glucose, amino acids, etc. as raw materials to produce cinnamic acid via the metabolism of *Rhodotorula* sp. OMK-1. The present invention provides a safe and environmentally friendly method for producing natural cinnamic acid at low temperature and low pressure with simple operation and reduced pollution.

4 Claims, 2 Drawing Sheets

YEAST STRAIN AND METHOD FOR PRODUCING NATURAL CINNAMIC ACID USING THE YEAST STRAIN FOR FERMENTATION

FIELD OF THE INVENTION

The present invention relates to a yeast strain and a method for producing natural cinnamic acid via the fermentation of the yeast strain.

BACKGROUND OF THE INVENTION

Cinnamic acid, also known as β-cinnamylic acid, 3-phenyl-2-acrylic acid, is a powder form with Cinnamon aroma. The color of cinnamic acid ranges from white to light yellow. The molecular weight is 148.17. The melting point is 133° C. The boiling point is 300° C. The specific gravity is 1.245. The refractive index is 1.555 (20° C.). Cinnamic acid is soluble in ethanol and methanol; highly soluble in benzene, acetic acid, petroleum ether, carbon disulfide and oil; slightly soluble in water. Natural cinnamic acid is mainly used in flavors and fragrances, food additives, pharmaceutical industry, beauty products and so on:

1, flavors and fragrances: natural cinnamic acid can be used as aromatic ingredient in soap, shampoo, detergent and cosmetics.

Cinnamic acid itself is a kind of spice with good aroma retention ability, Cinnamic acid as a raw fragrant ingredient, usually functioning as an auxiliary material, can make the fragrance of the main spices more dedicate and volatile. Cinnamic acid esters (such as methyl, ethyl, propylester, butyl ester) can be used as fixatives in beverages, cold drinks, candy, wine and other foods.

Cinnamic acid can be biosynthesized to L-phenylalanine by microbial enzyme. L-phenylalanine is an important food additive—the chief raw materials of Sweet aspartame (Aspartame).

2, food additives: cinnamic acid can be biosynthesized to L-phenylalanine by microbial enzyme. L-phenylalanine is an important food additives—the main raw materials of Sweet aspartame (Aspartame).

In WO0187080 (2001,11.22), Unilever introduced a cinnamic acid with essential oils and pasteurized adjuncts preservative system, which had a strong fungicidal and anti-corrosion effect. The preservative function of the cinnamic acid can be applied to preserve the food, vegetables and fruits. Cinnamic acid can also be used to improve the taste and flavor of canned fruit. As a food preservative, the cinnamic acid is harmless and environmentally friendly. As an alternative of sodium benzoate, potassium sorbate and other products, cinnamic acid can also be used in wine to make it more fresh and bright.

3, Pharmaceutical industry: cinnamic acid can be used for synthesizing baclofen and cinnarizine, which are important drugs for treating coronary heart disease. Cinnamic acid is also used in the manufacture of Prenylamini Lactas, Mepramidil, XinAn (a drug for heart disease), local anesthetic, bactericide, hemostatics etc. Cinnamic acid can also be used for spinal relaxants and antispasmodics. Cinnamic acid is mainly used for cerebral thrombosis, cerebral arteriosclerosis, coronary atherosclerosis and other diseases. Cinnamic acid can be used for inhibiting the proliferation of lung adenocarcinoma cells. Cinnamic acid is an effective inhibitor for A-5491 human lung adenocarcinoma cell giving great application value in anticancer.

4, Beauty products: tyrosine enzyme is the key enzyme in melanin synthesis, which starts the chain reaction of transferring the tyrosine into melanin biopolymers. Cinnamic acid inhibits the formation of tyrosine enzyme and has a certain role in blocking out UV, which can make the speckle shallower or even disappeared in one aspect. Cinnamic acid is one of the essential components in high-grade sunscreen. Cinnamic acid has a significant antioxidant effect on slowing down the appearance of wrinkles. Cinnamic acid also has good aroma retention ability, usually as a raw fragrant ingredient and a flavoring agent in daily use chemical essence.

There are many methods for the synthesis of cinnamic acid. The main synthesis methods are as follows: 1) Perkin synthesis; 2) benzaldehyde-acetone method; 3) benzyl chloride-anhydrous sodium acetate method; 4) Oxidate cinnamic aldehyde into cinnamic acid method. Method 1), 2) and 3) have the disadvantages of long process, high temperature, large energy consumption, low yield, more byproducts, difficult to separate and purify and heavy pollution. Method 4) uses $H_2O_2$ (required concentration is from 90% to 100%, making it dangerous goods), $NaClO_2$ and other inorganic oxide as oxidant for oxidation and uses a large number of organic solvents such as benzene and propionitrile, causing environmental pollution, which make method 4) difficult to commercialize.

SUMMARY OF THE INVENTION

The main object of the invention is to provide the use of a yeast strain and a method for producing natural cinnamic acid.

The object of the invention is achieved by:

The invention provides a strain of *Rhodotorula* sp. OMK-1, which was screened out from the soil from a cinnamon plantation. The yeast strain has been preserved at the China Center for Type Culture Collection, Wuhan University, Wuhan, Hubei Province on May 27, 2015, with the preservation number of CCTCC M 2015326. The yeast strain has the ability to produce natural cinnamic acid and is used in the production of natural cinnamic acid.

The use of the aforementioned yeast strain, *Rhodotorula* sp. OMK-1, is characterized in that it is used for the production of natural cinnamic acid.

A method for producing natural cinnamic acid is characterized in that it is produced by fermentation.

A method for producing natural cinnamic acid is comprised of the following steps:

1) strain activation: under aseptic conditions, a full inoculation loop of fungal liquid from the glycerol stock tube is evenly spread on agar slants, after which the agar slants are cultured in a biochemical incubator at 26-30° C. for 24-48 hours; wherein the aforementioned fungal liquid contains the strain *Rhodotorula* sp. OMK-1; the agar slants consist of the following components: glucose 1.0-3.5%, $KH_2PO_4$ 0.1-1.0%, NaCl 0.05-0.3%, yeast extract powder 0.1-1.0%, 2) seed culture: under aseptic conditions, a full inoculation loop of the well-grown cells from the aforementioned ager slants is inoculated onto a seed culture medium; the initial pH value of the seed culture medium is 5-8; under the growth conditions of 28-35° C. and 200-500 rpm rotational speed; cells are cultured until exponential growth phase; the seed culture medium comprises the following components: glucose 1.0-3.5%, $KH_2PO_4$ 0.1-1.0%, urea 0.1-0.6%, $MgSO_4$ 0.05-0.5%, NaCl 0.05-0.3%, corn syrup 0.1-1.0%, 3) fermentation: the cells in exponential growth phase are inoculated into a fermentation medium with volume ratio of 5-15% under aseptic conditions; the initial pH of the fermentation medium is 6.8-7.2; under the growth conditions of 30-40° C., 200-500 rpm rotational speed and 1:0.5 ventilation, the cells are fermented for 70-100 hours; the fermentation medium comprises the following components: glucose 2.0-5.0%, $KH_2PO_4$ 0.1-0.5%, urea 0.1-0.5%, $MgSO_4$ 0.05-0.5%, NaCl 0.05-3%, yeast extract 0.1-1.0%, $(NH_4)_2SO_4$ 0.1-0.5%, phenylalanine 1.0-2.0%.

4) extraction: extracting the natural cinnamic acid from the aforementioned fermentated medium.

In the preferred embodiment of the invention wherein step 4) comprises: after the completion of the fermentation process, the fermentation liquid is heated to inactivate the fungi; the cells are then filtered out by ceramic membrane; the natural cinnamic acid is extracted from the membrane filtrate by organic solvent, or the membrane filtrate is concentrated, after which the concentrate is acidated and crystallized under low temperature to separate and purify the natural cinnamic acid.

In the preferred embodiment of the present invention, the fermentation liquid is heated to 60-90° C.

The invention produces the natural cinnamic acid through fermentation. Glucose, amino acids and other natural raw materials are used as feedstock to produce the target product by microbial metabolism. The process is a safe and environmentally friendly production method, with the advantage of low temperature, low pressure, simple operation and reduced pollution.

PREFERRED EMBODIMENTS OF THE INVENTION

1, Strains

Figure 1A:
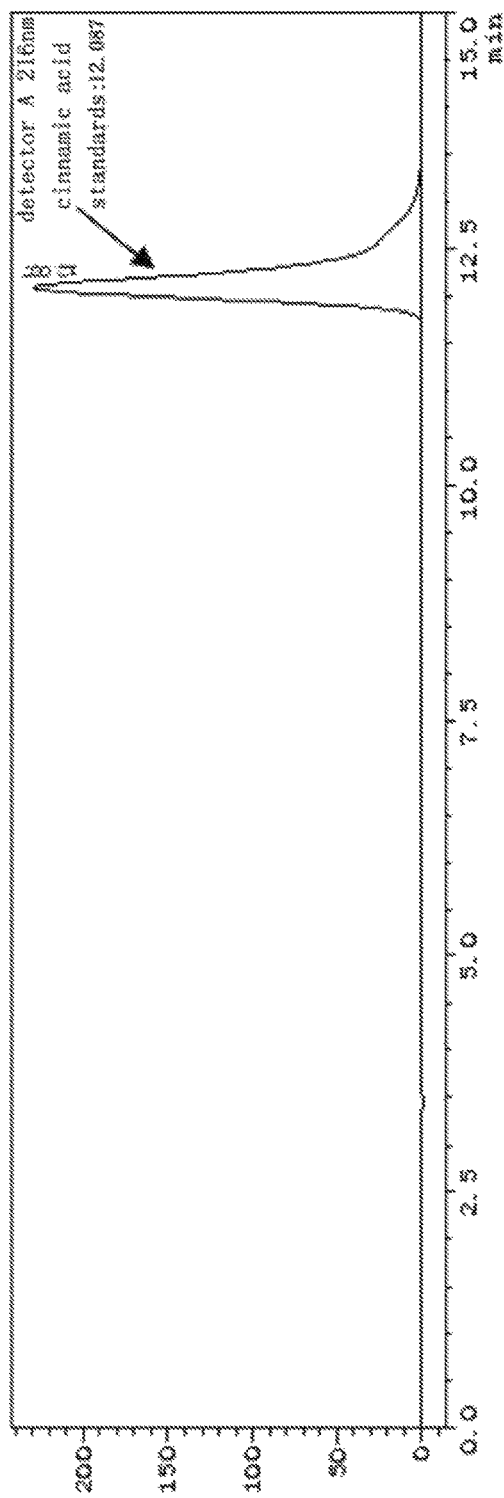
FIG. 1A is the HPLC chromatogram of cinnamic acid in embodiment 3.

The strain *Rhodotorula* sp. OMK-1 capable of producing natural cinnamic acid was isolated from the soil of cinnamon plantation forest, Haikou, Hainan Province, China. The strain has been preserved at the China Center for Type Culture Collection, Wuhan University, Wuhan, Hubei Province on May 27, 2015, with the preservation number of CCTCC M 2015326.

The cells are oval and the colonies are orange and round, with a smooth edge and smooth surface. The strain is able to metabolize glucose, sucrose, ribose and Arabia sugar, but the strain is not able to metabolize L-sorbitol, maltose and red sugar alcohol. The 18S and 26S rRNA sequences of the strain have 99% similarity with the 18S and 26S rRNA sequences of the red yeast standard strain, so the strain is identified as a species from the *Rhodotorula* genus.

2, Strain Activation

Under aseptic conditions, a full inoculation loop of fungal liquid from the glycerol stock tube is evenly spread on agar slants, after which the agar slants are cultured in a biochemical incubator at 28-30° C. for 24-48 hours. The agar slants consist of the following components: glucose 1.0-3.5%, $KH_2PO_4$ 0.1-1.0%, NaCl 0.05-0.3%, yeast extract powder 0.1-1.0%.

3, Seed Culture

Under aseptic conditions, a full inoculation loop of the well-grown cells from the aforementioned ager slants is inoculated onto a seed culture medium. The initial pH value of the seed culture medium is 5-8, under the growth conditions of 28-35° C. and 150-500 rpm rotational speed. Cells are cultured until exponential growth phase. The seed culture medium comprises the following components: glucose 1.0-3.5%, $KH_2PO_4$ 0.1-1.0%, urea 0.1-0.6%, $MgSO_4$ 0.05-0.5%, NaCl 0.05-0.3%, corn syrup 0.1-1.0%.

4, Fermentation Process

The cells in exponential growth phase are inoculated into a fermentation medium with volume ratio of 10% under aseptic conditions. The initial pH of the fermentation medium is 7.0, under the growth conditions of 30-40° C., 200-500 rpm rotational speed and 1:0.5 ventilation. The cells are fermented for 70-120 hours. The fermentation medium comprises the following components: glucose 2.0-5.0%, $KH_2PO_4$ 0.1-0.5%, urea 0.1-0.5%, $MgSO_4$ 0.05-0.5%, NaCl 0.05-3%, yeast extract 0.1-1.0%, $(NH_4)_2SO_4$ 0.1-0.5%, phenylalanine 1.0-2.0%.

5, Extraction Process

After the completion of the fermentation process, the fermentation liquid is heated to 80° C. to inactivate the fungi. The cells are then removed by filtration with ceramic membrane. The membrane filtrate is either extracted by organic solvent (such as ethyl acetate), or the membrane filtrate was acidated to crystallize and separate the natural cinnamic acid.

Embodiment 1: Production of Natural Cinnamic Acid (Flask Shaking Fermentation)

Preparation of the seed culture medium: the seed culture medium composition was as follows (g/L): glucose 30, $KH_2PO_4$ 5, urea 4, $MgSO_4$ 0.8, NaCl 2.5, corn syrup 5, urea 6 and water as solvent; the initial pH was 7.0; the seed culture medium was sterilized for 30 minutes at 121° C.

Preparation of the fermentation medium: the fermentation medium composition was as follows (g/L): glucose 30, $KH_2PO_4$ 5, urea 5, $MgSO_4$ 0.6, yeast extract 8, $(NH_4)_2SO_4$ 3, phenylalanine 30 and water as solvent; initial pH was 7.0; the fermentation medium was sterilized for 30 minutes at 121° C.

Seed preparation: under aseptic conditions, the strain of *Rhodotorula* sp. OMK-1 in low temperature glycerol tube was transferred into fresh, sterile culture plate for activation at 28° C. for 2 days; then the fungal colonies were selected and inoculated into a 500 mL flask for seed culture, where the volume of the medium was 50 mL and the rotation speed was 180 rpm at 30° C.; seed liquid was acquired after 24 hours of growth.

The fermentation of natural cinnamic acid: 50 mL of the prepared fermentation medium was poured into a 500 mL sterile triangle flask, and 7.5 mL of acquired seed liquid was inoculated into the same flask for fermentation; the fermentation temperature was 30° C.; the rotation speed was 200 rpm. After being fermented for 100 hours, the concentration of the cinnamic acid in the fermentation broth measured by HPLC method was 15 g/L.

Embodiment 2: Production of the Natural Cinnamic Acid (Stirred Reactor Fermentation)

The seed culture medium and the fermentation medium were prepared as described in embodiment 1.

Seed preparation: under aseptic conditions, the strain of *Rhodotorula* sp. OMK-1 in low temperature glycerol tube was transferred into a fresh, sterile medium plate, for activation at 28° C. for 2 days; fungal colonies were selected and inoculated into a 3 L tank equipped with 1.8 L of seed medium. The tank was incubated with ventilation at 30° C., stirring speed of 300 rpm, obtaining seed liquid after 24 hours of culture.

The fermentation of the natural cinnamic acid: 10.2 L of the prepared fermentation medium was added into a 20 L fermentor; the fermentor with the fermentation medium was sterilized at 121° C. for 30 min, after which 1.8 L of cultured seed liquid was added into the 20 L fermentor for fermentation with fermentation temperature at 30° C., stirring speed of 400 rpm. Ventilation ratio was 1:0.2. The fermentation cycle was 110 hours. At the end of fermentation, the concentration of the natural cinnamic acid in fermentation broth measured by HPLC method was 20 g/L.

Figure 1B:
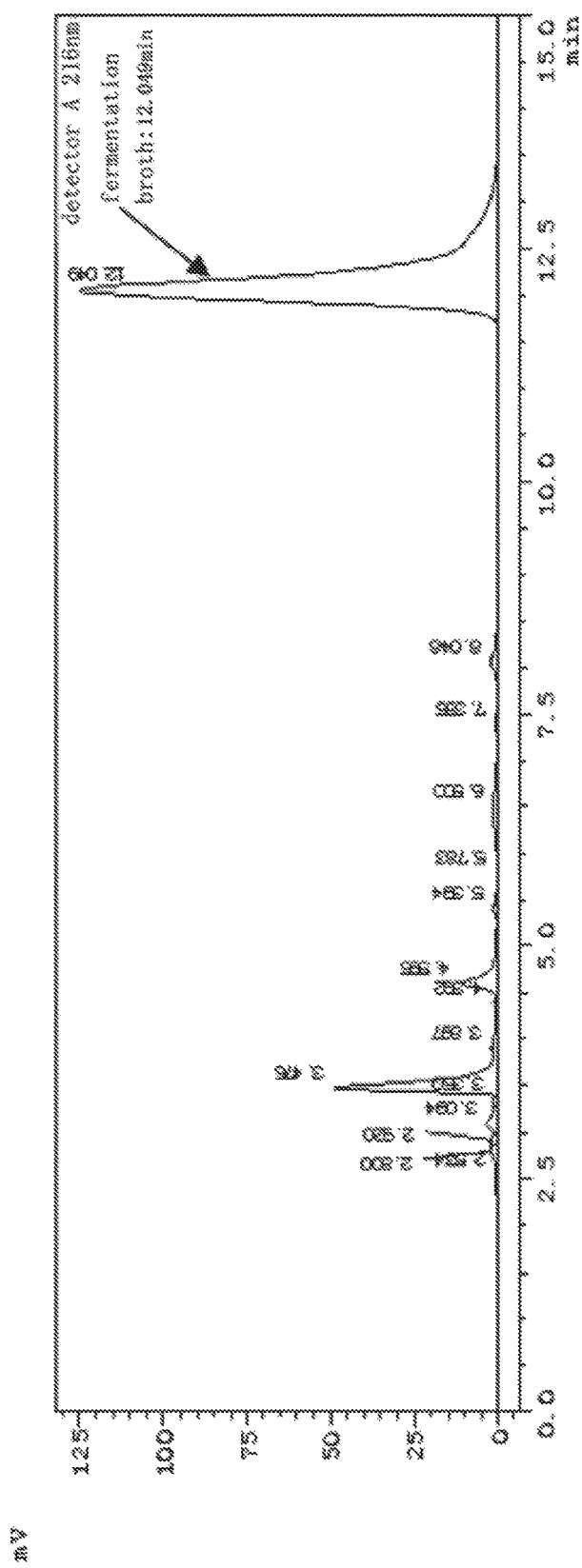
FIG. 1B is the HPLC chromatogram of fermentation broth in embodiment 3, the results show that the product is the natural cinnamic acid.

Embodiment 3: Extraction of the Natural Cinnamic Acid 50 mL of fermentation broth of embodiment 1 was pasteurized at 80° C. in a water bath for 30 min for sterilization. The fermentation broth was centrifuged to separate out the fungi at 5000 rpm, and the pH was adjusted to 3-5 with dilute acid. The fermentation broth was then stood for 5 min, after which 50 mL of ethyl acetate was added to layer the fermentation broth. Organic phase layer was dried in a rotary evaporator to evaporate the ethyl acetate. At last, 0.7 g of dry natural cinnamic acid production was obtained. The HPLC figure was shown in FIG. 1A and FIG. 1B.

Embodiment 4: Extraction of the Natural Cinnamic Acid

12 L of fermentation broth in embodiment 2 was taken to filtration by ceramic membrane at 60° C. Ten liter of filtrate was gathered and adjusted to pH of 3-5 with dilute acid. The acidified filtrate was stood for 4 hours, centrifuged and dried. Finally 216 g of natural cinnamic acid was obtained.

INDUSTRIAL APPLICABILITY

The method of the invention is by fermentation at low temperature and low pressure. The process is relatively safe and the operation is simple.

What is claimed is:

1. A method for producing natural cinnamic acid using the strain *Rhodotorula* sp. OMK-1 having preservation number CCTCC M 2015326, wherein the method comprises the steps of:
   1) strain activation;
   2) seed culture; and
   3) fermentation to produce natural cinnamic acid.

2. The method for producing natural cinnamic acid according to claim 1,
   wherein strain activation step 1 comprises:
      under aseptic conditions, a full inoculation loop of *Rhodotorula* sp. OMK-1 from a glycerol stock tube is evenly spread on agar slants, after which the agar slants are cultured in a biochemical incubator at 26-30° C. for 24-48 hours; wherein the agar slants include the following components: glucose 1.0-3.5%, KH2PO4 0.1-1.0%, NaCl 0.05-0.3%, and yeast extract powder 0.1-1.0%, and
   wherein seed culture step 2 comprises:
      under aseptic conditions, a full inoculation loop of well-grown OMK-1 cells from step 1 is inoculated onto a seed culture medium having an initial pH value of 5-8; under growth conditions of 28-35° C. with rotation at 200-500 rpm until exponential growth is reached; wherein the seed culture medium comprises: glucose 1.0-3.5%, KH2PO4 0.1-1.0%, urea 0.1-0.6%, MgSO4 0.05-0.5%, NaCl 0.05-0.3%, and corn syrup 0.1-1.0%, and
   wherein fermentation step 3 comprises:
      the cells from step 2 in exponential growth phase are inoculated into a fermentation medium with volume ratio of 5-15% under aseptic conditions having an initial pH of 6.8-7.2 at 30-40° C., with rotation at 200-500rpm and 1:0.5 ventilation for 70-100 hours to achieve fermentation; wherein the fermentation medium comprises: glucose 2.0-5.0%, KH2PO4 0.1-0.5%, urea 0.1-0.5%, MgSO4 0.05-0.5%, NaCl 0.05-3%, yeast extract 0.1-1.0%, (NH4)2SO4 0.1-0.5%, and phenylalanine 1.0-2.0%.

3. The method for producing natural cinnamic acid according to claim 2, further comprising step 4 wherein after step 3, the fermentation liquid is heated to inactivate the OMK-1 cells; and thereafter the cells are filtered out using a ceramic membrane; wherein the natural cinnamic acid is extracted from the ceramic membrane filtrate by an organic solvent, or the ceramic membrane filtrate is concentrated and acidified at low temperature to separate and purify the natural cinnamic acid.

4. The method for producing natural cinnamic acid according to claim 3,
   wherein the fermentation liquid is heated to 60-90° C. to inactivate OMK-1 cells.

* * * * *